US006765198B2

(12) United States Patent
Jenkins et al.

(10) Patent No.: US 6,765,198 B2
(45) Date of Patent: Jul. 20, 2004

(54) ENHANCEMENTS TO ION MOBILITY SPECTROMETERS

(75) Inventors: Anthony Jenkins, North Reading, MA (US); William J. McGann, Raynham, MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/103,601

(22) Filed: Mar. 20, 2002

(65) Prior Publication Data

US 2002/0134933 A1 Sep. 26, 2002

Related U.S. Application Data

(60) Provisional application No. 60/277,318, filed on Mar. 20, 2001.

(51) Int. Cl.[7] .......................... H01J 49/40; H01J 49/00
(52) U.S. Cl. ..................... 250/287; 250/282; 250/288; 250/286; 250/379; 250/382
(58) Field of Search ................................. 250/281–282, 250/286–288, 290, 293

(56) References Cited

U.S. PATENT DOCUMENTS

| 3,621,240 A | * | 11/1971 | Martin ........................ 250/282 |
| 3,742,213 A | * | 6/1973 | Cohen et al. ................ 250/282 |
| 3,845,301 A | * | 10/1974 | Wernlund et al. ........... 250/287 |
| 3,845,304 A | | 10/1974 | Tamura et al. |
| 5,200,614 A | * | 4/1993 | Jenkins ........................ 250/286 |
| 5,475,217 A | * | 12/1995 | Bradshaw .................... 250/287 |

FOREIGN PATENT DOCUMENTS

EP          551722 A1 *   7/1993   .......... G01N/27/64

* cited by examiner

Primary Examiner—Nikita Wells
Assistant Examiner—Christopher M. Kalivoda
(74) Attorney, Agent, or Firm—Anthony J. Casella; Gerald E. Hespos

(57) ABSTRACT

An ion trap mobility spectrometer is provided. The ion trap mobility spectrometer employs algorithms to simultaneously detect and analyze both positive and negative plasmagrams. Selectivity is improved by detecting the presence of peaks in both spectra and setting logic filters which require the presence or absence of certain peaks in both spectra. Selectivity is improved by looking for two peaks in the two spectra.

15 Claims, 4 Drawing Sheets

ELECTRIC POTENTIAL DOWN THE DRIFT TUBE

ENHANCEMENTS TO ION MOBILITY SPECTROMETERS

This application claims priority on U.S. Provisional Patent Appl. No. 60/277,318, filed Mar. 20, 2001.

BACKGROUND OF THE INVENTION

1. Field of the Invention

The subject invention relates to an ion mobility spectrometer for detecting trace amounts of materials of interest.

2. Description of the Related Art

Ion mobility spectrometry was first reduced to practice in the early to mid 1970's for the detection and identification of samples carried into an ion mobility spectrometer (IMS) on a stream of clean dry air. Examples of prior art ion mobility spectrometers are shown in U.S. Pat. No. 3,621,240 to Cohen et al., U.S. Pat. No. 3,742,213 to Cohen et al. and U.S. Pat. No. 3,845,301 to Wernlund et al. The IMS described in early literature and patents was capable of distinguishing between ionic species that differed by about ten atomic mass units, but this also depended on molecular shape factors. Further selectivity was achieved by the addition of dopant vapors in the gas stream entering the detector. Typically the dopant would have a charge affinity intermediate that of the target materials and the majority of commonly occurring materials that are of no interest.

The ion trap mobility spectrometer was developed in 1992 and is shown in U.S. Pat. No. 5,200,614 which issued to Jenkins. The ion trap mobility spectrometer allows ion populations longer time in the zero field reaction region of the detector. This facilitates transfer of charge between initially generated ionic species in the detector and the dopant materials. Subsequent charge transfer from the dopant ion to target ions of stronger charge affinity was similarly facilitated in the zero field environment of the detector chamber of the ITMS. U.S. Pat. No. 5,491,337 described the use of ammonia as dopant ion for narcotics detection.

The ITMS has been successfully deployed to detect explosives in the negative ion mode and narcotics in the positive ion mode of operation. It is possible to switch modes of operation by switching the direction of the electric field in the drift region of the detector. A full description of the detector and electrical connection of the ITMS is given in U.S. Pat. No. 5,200,614. Briefly, the ITMS operates by first trapping traces of vapor or particles given off or left behind by explosives and/or narcotics. These trapped samples are vaporized and drawn into the detection system where they are analyzed by a detection system that provides almost 100 times more sensitivity than any prior ion mobility spectrometers. The ITMS ionizes the target vapors and then measures the mobility of the ions in an electric field. The mobility of each target ion differs sufficiently so that each is uniquely identified. This process can take less than three seconds to complete.

Samples are collected on clean paper sample traps either by air sampling with a hand held vacuum sampler or simply wiping suspect surfaces with the trap. Any vapors or microscopic particles of target materials collected on the trap are introduced into the detection system by placing the sample trap in the heated desorption unit shown in FIG. 1. Desorbed vapors are drawn into the ITMS by the action of a small sampling pump. The sampled air leaving the desorption unit is drawn over a semipermeable, elastomeric membrane that allows target vapors to permeate into the detection system. Dust and dirt is excluded by the membrane, thus, protecting the detector from contamination.

The sample molecules that pass through the membrane are carried into the detector in a stream of clean, dry air that is circulated by a small pump (see FIG. 1). The carrier gas with the vaporized sample proceeds through an ionization chamber where both positive and negative ions are formed.

The electric field in the detector's reaction chamber is at most times zero, but at 20 mS intervals, short pulses are applied across the chamber. This pulsed electric field forces the sample, now in an ionized gas state, to proceed towards the collector electrode. The speed of the ion is related to its size and mass, thus, a measurement of this speed makes substance identification possible. The collector and related electronics pass a constant stream of analogue information from the ITMS into the system computer for digital conversion, analysis and identification.

The ITMS provides high sensitivity due to the increased ionization efficiency compared with standard ion mobility spectrometers. Additionally, detector selectivity is enhanced by the use of the semipermeable membrane in the sampled air stream before the detector. Many organic vapors are transmitted through the membrane and could produce unwanted responses in the detector. These responses are eliminated by the addition of a trace of dopant vapor in the gas stream entering the detector. The dopant is carefully chosen to ensure that it will steal all charge from unwanted ions, and in the absence of narcotics (or explosives in negative ion mode) will produce a single response peak in the spectrum. These are sequentially measured, and produce a positive ion spectrum or plasmagram. Similarly a negative ion spectrum is produced in the negative ion mode for explosives detection.

The time taken to switch modes between positive and negative electric fields in existing equipment is approximately ten seconds. This time is determined by the speed at which the very high voltages employed in the drift region can be discharged and reversed. Unfortunately the residence time of a sample in the detector system is only about five to ten seconds. This is due to the nature of the desorption of particulate samples in the desorber of the product. It is not therefore possible to generate both a positive and negative ion spectrum from the same sample with prior art equipment. The present invention addresses the need to generate positive and negative ion spectra from the same sample and provides a convenient and elegant solution.

Hitherto, there has been little demand for a detector system that would simultaneously detect narcotics and explosives. It would however be helpful in a few applications such as inspection of packages entering the country. The greatest advantage to being able to detect both negative and positive ion spectra from the same sample is to improve both detection capability and selectivity. For example, when providing routine screening of airline passengers and baggage it is important to detect all possible terrorist explosives. Unfortunately there are a few rare explosives that are not very sensitive in the negative ion mode but are more responsive in the positive ion mode. Improved security is achieved by monitoring both positive and negative ion spectra.

In narcotics or positive mode of operation the range of charge affinity that is allowed by the dopant chemistry is greater than is allowed in the negative ion mode. This means that there are more interfering compounds in the narcotics mode than in explosives mode. Unfortunately false positive responses in narcotics mode are procedurally more problematic than explosives false positives. The reverse is true for false negatives. (It would be disastrous to allow a bomb on board an aircraft.) Interdiction forces are already missing 90% of the narcotics entering the country so a few false negatives are not of great concern. Simply put, more selectivity in narcotics detection and more detection capability (sensitivity) in explosives detection is desired. The present invention addresses both these requirements.

Chemical warfare agents are either strongly electropositive or strongly electronegative. Any IMS system designed for the full range of chemical weapons threat must be able to detect both positive and negative ion spectra simultaneously. The present invention would be particularly applicable to chemical warfare agent detection.

SUMMARY OF THE INVENTION

The invention is directed to an improved ion trap mobility spectrometer and a method for testing for the presence of at least one substance of interest in a sample of air. The spectrometer includes a desorber for receiving a sample trap that has been placed in communication with a potential source of substances of interest. A pump is provided for directing a flow of air across the sample trap for delivering substances on the sample trap from the desorber to an ionization chamber. A drift chamber is disposed adjacent the ionization chamber and a collector electrode is disposed at an end of the drift chamber remote from the ionization chamber. A plurality of sequentially spaced grid electrodes are disposed in the drift chamber between the ionization chamber and the collector electrode.

The ionization chamber functions to bombard molecules in the sample gas to produce ionized molecules. At most times, the electric field in the ionization chamber is zero. However, short pulses are applied across the chamber to propel the ionized gas from the ionization chamber into the drift chamber. The grid electrodes in the drift chamber are operated at a first polarity for a first selected period of time to cause at least a first species of molecules to be directed toward the collector electrode. The collector electrode is connected to a signal processor and a display means. The signal processor identifies at least the first species of molecules impinging thereon. A display means then produces at least one plasmagram for identifying at least certain species of ions, as collected on the collector electrode and analyzed by the signal processor.

The ion trap mobility spectrometer further includes switching means for rapidly reversing polarity of the grid electrodes. The reverse of polarity may propel other species of ions toward the collector electrode. In this manner, a single sample of air drawn from a single sample trap can be analyzed for two different species of substances of interest or can be analyzed to assess more accurately the presence of certain species of substances of interest that may have other molecules that can be detected better in a positive mode as well as molecules that can be detected in a negative mode.

DETAILED DESCRIPTION OF THE PREFERRED EMBODIMENTS

Figure 1:
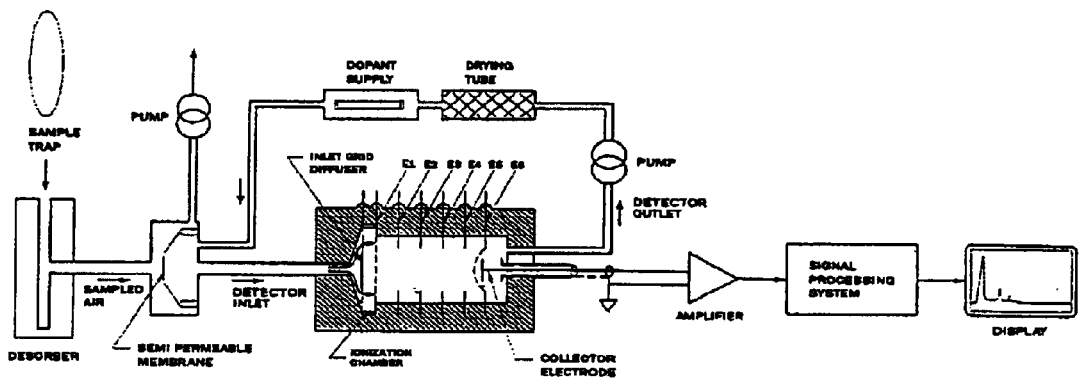
FIG. 1 is a schematic cross-section of an ion trap mobility spectrometer detection system.
Figure 2:
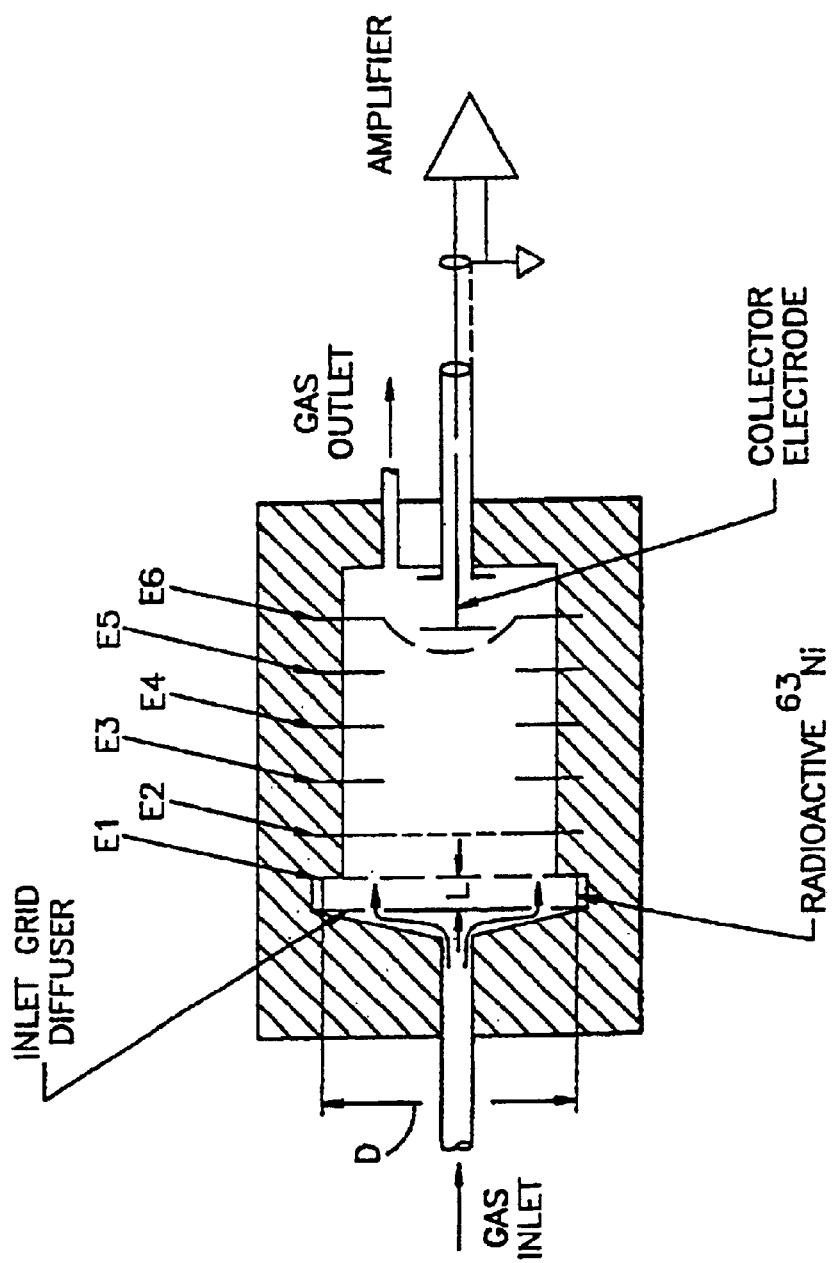
FIG. 2 is a cross-sectional view of a detector in accordance with the subject invention.
Figure 3:
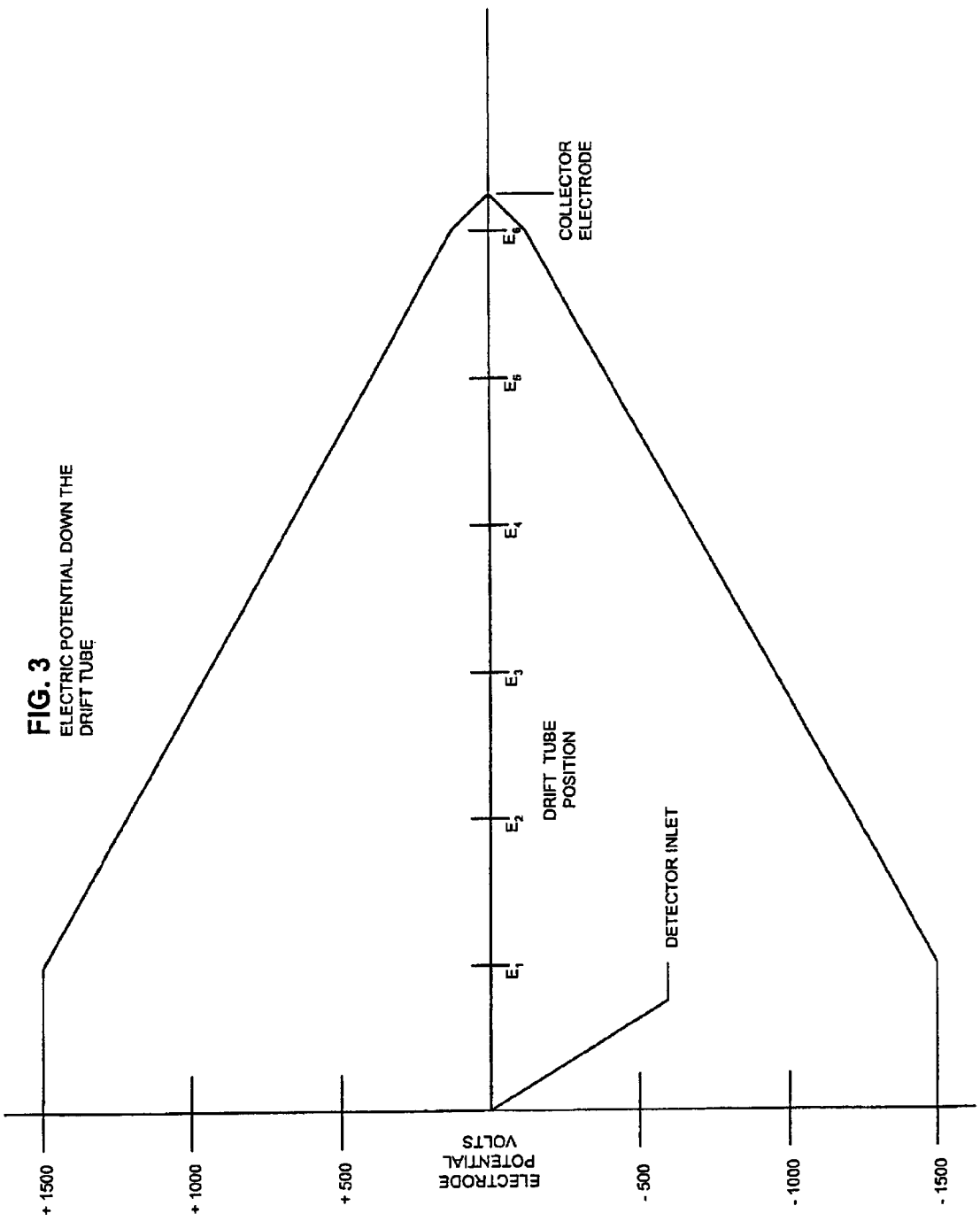
FIG. 3 shows the electric potential at various points within the ITMS detector during the ion drift.

The reaction region of the ITMS detector described in U.S. Pat. No. 5,200,614, and shown in FIG. 2, is, for most of the detection cycle, a field free space. In other words all the internal conductive surfaces are at the same electric potential and there are equal numbers of positive and negative charges within the chamber. It is immaterial what voltage is applied to the internal conductive surfaces provided all are at the same potential. The electric potential can therefore be changed without affecting the ions in the chamber. FIG. 3 shows the electric potential at various points within an existing ITMS detector during the ion drift period. The upper curve shows the potential during positive ion mode and the lower curve, the negative ion mode. In the existing ITMS shown in FIG. 2, the ionic population is allowed to build up for about 20 mS at which time an electric field is applied across the reaction chamber and ions of interest are expelled through the first grid E1, down the drift section E2–E6 to the collector electrode. In one existing ITMS the ion drift process typically takes two or three milliseconds for the lightest ions and about 12 mS for the heaviest ions of interest. A few milliseconds further are allowed to ensure that all heavy ions are removed from the detector and the whole process is repeated. In the subject invention, at this point the polarity of the electric field down the drift tube is reversed changing from one curve to the other of FIG. 3.

Figure 4:
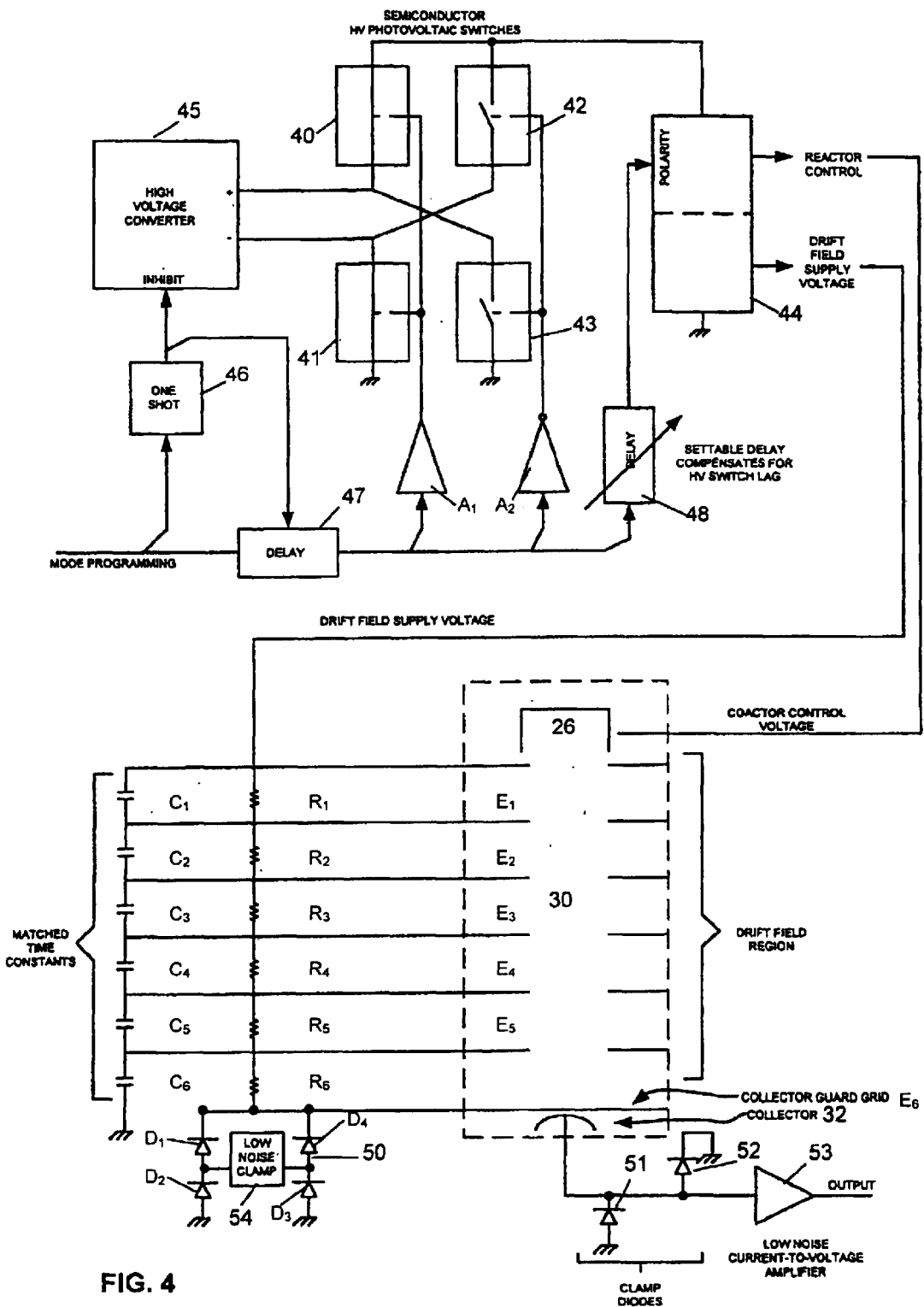
FIG. 4 is an electronic circuit diagram showing the switching circuit of the invention.

The electronic circuit shown in FIG. 4 achieves the polarity switch. It is essential that the transition is accomplished in a short time so that as few ions and as little time as possible is lost during the transition. The switching circuit shown in FIG. 4 is one embodiment of the invention that is capable of switching the very high voltages from positive to negative and vice versa in a few milliseconds or less. The transient disturbance caused in the signal amplification circuit due to capacitative coupling of the collector guard grid and the collector itself must be reduced to a minimum in order that the signal recovers within a very short period of a few milliseconds. Capacitative effects at the collector electrode and pre-amplifier shown in FIG. 4 must be kept as a low as possible, preferably below 1 nano farad in order to achieve rapid dissipation of the transient signal.

When positive drift conditions exist, the ions that are collected are all positive ions. The ensuing ion current is fed into a digitizer where a digital temporal spectrum is generated and stored in memory. Subsequent positive ion spectra can be summed in discrete sets of a few scans. This has the advantage of signal averaging random noise within the scan set. It is advantageous to change polarity for each scan because ionic populations and mix of ions change in subsequent scans after polarity switching.

When the polarity is switched, the ionic signal is stored in separate memory so that positive and negative plasmagrams are generated very nearly in real time, being delayed by only a fraction of a second. This in turn allows dynamic analysis simultaneously of each spectra.

In previous ion mobility spectrometers, the ion spectrum (plasmagram) was passed through peak detection and analysis algorithms. In negative ion mode, for example, explosive materials typically produce one and possibly more peaks in the spectrum at specific drift times in the spectrum. Peaks are detected in the plasmagram which are then compared to the expected peak positions of the explosive of interest. This method of analysis detects most explosives very sensitively (sub nanogram levels) and in use at airport security checks provides nuisance alarm rates typically below 1%.

In the present invention, new algorithms have been developed to simultaneously detect and analyze both positive and negative plasmagrams. Selectivity is improved by detecting the presence of peaks in both spectra and setting logic filters which require the presence or absence of certain peaks in both spectra. Peak strength ratios from one spectrum to the other also provide a further filter where an interferent has similar peak positions to a targeted compound.

If the probability of finding an interferent in the window of a targeted compound is 0.1%, then the probability of finding another or the same interferent responding in a second window, statistically, is one in a million. By looking for two peaks in the two spectra, selectivity is dramatically improved.

The taggant material, which is used to tag plastic explosives in many countries, by international agreement, is di-methyl-di-nitro-butane (DMNB). This does not readily respond in negative ion mode, but is detected in positive ion mode. The present invention provides improved detection capability for several explosive and incendiary materials as well as the taggant, DMNB, which are not readily detected in negative ion mode.

Ion mobility spectrometers have not hitherto found use in medical diagnostics. Doctors however, have diagnosed infections and diseases by their own olfactory senses and diagnostic odors do exist. IMS and ITMS devices do not normally detect these odors since the dopant ion chemistry specifically inhibits the detection of most classes or organic compounds. Without the addition of dopant ion mobility spectrometers would exhibit very high false positive responses. This new improvement allows greater selectivity by choosing several identifying peaks in the two spectra and employing peak ratio selection criteria. This in turn allows operation without dopants which increases the range of materials that can be detected while providing reasonably low false positive responses. This new detection capability is expected to find application in medical diagnostics.

The semiconductor switch devices employed are limited in voltage capability; therefore four semiconductor switch devices 40–43 are arranged in a bridge circuit. For this reason a high voltage converter 45 with an isolated output also is used. Also, the switch devices 40–43 are limited in peak switching current capability; therefore the high voltage converter is first turned off when a mode change through one shot 46 is to be made. After a delay by unit 47, the drive through operational amplifiers A1 and A2 is removed from the switches that were on and applied to the ones that were off. This may be done simultaneously because the switch design guarantees that there is a longer delay for them to "make" than to "break".

At the same time the switch states are changed, the high voltage converter is turned on again to re-charge the output capacitances to the operating voltage.

The circuit (44, 47) that generates the pulse which is supplied to the reactor region of the detector depends on the polarity of its supply voltage; therefore this circuit must be switched at the same instant as the high voltage switches are changing state to avoid expelling ions from the reactor. For this reason an adjustable delay circuit 48 is inserted in the control to the high voltage pulser 44.

The circuit which supplies the voltages to the drift field electrodes uses resistors ($R_1$–$R_6$) to divide down the high voltage and capacitors ($C_1$–$C_6$) for filtering. These resistors and capacitors must be closely proportional in value to maintain the required drift field distribution immediately following mode switching.

The voltage applied to the collector guard grid $E_6$ must be completely stable following mode switching, and it must also be free of noise. This is accomplished with a clamp circuit 50 using a diode bridge ($D_1$–$D_4$) loaded with a large capacitance in parallel with a zener diode-series resistor combination 54. This clamp is fed with a resistor $R_6$ from the drift field resistor string. The positive or negative clamped voltage is connected to the collector guard grid $E_6$.

The current output from the collector electrode 32 now contains relatively large transient pulses during mode switching. The low noise transimpedance amplifier 53 must now have low capacitance clamping diode devices 51, 52 on its input to shunt these pulses and thus allow rapid recovery from switching.

What is claimed is:

1. A method for testing for the presence of a plurality of substances of interest in a single sample of air, said method comprising:

directing the sample of air into a substantially field free reaction chamber of an ion trap mobility spectrometer;

operating the ion trap mobility spectrometer at a first polarity for a first selected time for checking for the presence of ions of a first polarity indicative of at least a first substance of interest in the sample of air;

reversing the polarity of the ion trap mobility spectrometer within a selected transition time;

operating the ion trap mobility spectrometer at a reversed polarity for a second selected time for checking for the presence of ions of opposite polarity in the same sample of air, wherein a sum of the first selected time, the transition time and the second selected time being less than a maximum permissible residence time for the single sample of air in the ion trap mobility spectrometer.

2. The method of claim 1, wherein the first and second selected times each are less than approximately 20 mS and wherein the transition time is less than 10 mS.

3. The method of claim 2, wherein the first and second selected times are less than approximately 15 mS and wherein the transition time is less than approximately 5 mS.

4. A method for testing for the presence of at least one of a plurality of substances of interest in a sample of air, said method comprising:

providing an ion trap mobility spectrometer having an inlet for receiving the sample of air, an ionization chamber communicating with the inlet for ionizing molecules of the sample of air in the ionization chamber, the ionization chamber normally defining a substantially field free space, a drift chamber adjacent the ionization chamber, a collector electrode at a location in the drift chamber spaced from the ionization chamber and a plurality of grid electrodes sequentially spaced between said ionization chamber and said collector electrode;

directing the sample of air into the ionization chamber;

ionizing molecules in the sample of air;

operating the grid electrodes for a first selected time at a first polarity for directing at least a first species of the ionized molecules in the sample toward the collector electrode;

developing a first plasmagram for identifying at least certain of the first species of the ionized molecules;

reversing the polarity of the grid electrodes, said reversing of the polarity being carried out within a transition time;

operating the grid electrodes for a second selected time at the reversed polarity for directing at least a second species of the ionized molecules in the sample toward the collector electrode;

developing a second plasmagram for identifying at least certain of the second species of ionized molecules collected by the collector electrode, wherein a sum of the first selected time, the transition time and the second selected time being less than the maximum permissible residence time for the sample in the ion trap mobility spectrometer.

5. The method of claim 4, wherein the first and second selected times each are less than approximately 20 mS and wherein the transition time is less than 10 mS.

6. The method of claim 5, wherein the first and second selected times are less than approximately 15 mS and wherein the transition time is less than approximately 5 mS.

7. An ion trap mobility spectrometer comprising an inlet for receiving a sample of air, an ionization chamber communicating with the inlet for ionizing molecules of the sample of air, a drift chamber adjacent the ionization chamber, a collector electrode at a location in the drift chamber spaced from the ionization chamber, a plurality of grid electrodes sequentially spaced between said ionization chamber and said collector electrode for generating a charged field in the drift chamber, and a switch for reversing polarity of the grid electrodes, whereby the switch operates sufficiently fast for testing the sample of air in both a positive mode and a negative mode for at least one substance of interest.

8. The ion trap mobility spectrometer of claim 7, wherein the switch reverses polarity of the grid electrodes in less than about 10 mS.

9. The ion trap mobility spectrometer of claim 7, wherein the switch reverses polarity of the grid electrodes in less than about 5 mS.

10. The ion trap mobility spectrometer of claim 8, wherein said switch means further comprises a variable delay circuit element operationally coupling a high voltage supply to a high voltage pulsor, thereby enabling application of a variable delay in said high voltage supply.

11. The ion trap mobility spectrometer of claim 7, further comprising signal processor connected to said collector electrode for processing signals indicative of identity of ions impinging on the collector electrode and a display connected to said signal processor for producing plasmagram of output from said collector electrode during both said positive and negative polarities of said grid electrodes.

12. The ion trap mobility spectrometer of claim 7, wherein the switch comprises a plurality of semiconductor switch devices arranged in a bridge circuit limited in peak switching current capability and having a longer delay in making a switch than in breaking a switch.

13. The ion trap mobility spectrometer of claim 12, wherein said switch further comprises a high voltage converter coupled to said bridge circuit and having an isolated output.

14. The ion trap mobility spectrometer of claim 13, wherein the switch further comprises voltage polarity switch coupled between a high voltage supply and said high voltage converter for turning off said high voltage converter when a mode change is to be made between a positive and a negative voltage, said voltage polarity switch comprising a delay circuit for removing a driving voltage from the semiconductor switch devices that are on and applying said voltage with a delay to the semiconductor switch devices that are off and substantially simultaneously turning the high voltage converter on again to alternately provide a positive and a negative high voltage outlet from said bridge circuit.

15. The ion trap mobility spectrometer of claim 14, wherein said switch further comprises a high voltage pulsor having inputs from said bridge circuit and said high voltage supply and producing outputs responsive to positive and negative high voltage switching for providing a drift field supply voltage to said grid electrodes and a control voltage to said ionizing chamber, said voltage alternately switching between positive and negative high voltages.

* * * * *